(12) United States Patent
Jooris et al.

(10) Patent No.: US 9,675,974 B2
(45) Date of Patent: Jun. 13, 2017

(54) CAP FOR MONITORING OBJECTS IN SUSPENSION

(71) Applicant: Ovizio Imaging Systems NV/SA, Brussels (BE)

(72) Inventors: Serge Jooris, Gistoux (BE); Philip Mathuis, Asse (BE)

(73) Assignee: Ovizio Imaging Systems NV/SA, Brussels (BE)

( * ) Notice: Subject to any disclaimer, the term of this patent is extended or adjusted under 35 U.S.C. 154(b) by 0 days.

(21) Appl. No.: 14/909,046

(22) PCT Filed: Jul. 29, 2014

(86) PCT No.: PCT/EP2014/066312
§ 371 (c)(1),
(2) Date: Jan. 29, 2016

(87) PCT Pub. No.: WO2015/014858
PCT Pub. Date: Feb. 5, 2015

(65) Prior Publication Data
US 2016/0184817 A1   Jun. 30, 2016

(30) Foreign Application Priority Data
Jul. 31, 2013 (EP) ..................................... 13178714

(51) Int. Cl.
*B01J 10/00* (2006.01)
*G01N 15/06* (2006.01)
(Continued)

(52) U.S. Cl.
CPC ........... *B01L 3/50273* (2013.01); *B01L 3/502* (2013.01); *B01L 3/502715* (2013.01);
(Continued)

(58) Field of Classification Search
CPC ........ B01L 3/14; B01L 3/50273; B01L 3/502; B01L 3/502175; B01J 10/00; G01N 15/06; G01N 21/00
(Continued)

(56) References Cited

U.S. PATENT DOCUMENTS 5,243,409 A * 9/1993 Sagner .......................... 356/436
6,809,862 B2 10/2004 Behnsen et al.
(Continued)

FOREIGN PATENT DOCUMENTS

CN   202 808 799   3/2013

OTHER PUBLICATIONS

International Search Report—PCT/EP2014/066312—ISA/EPO—mailed Jan. 10, 2014.

*Primary Examiner* — Brian J Sine
(74) *Attorney, Agent, or Firm* — Knobbe Martens Olson & Bear, LLP (57) ABSTRACT

A vessel is for storing and monitoring a suspension of microscopic objects, which comprises a cap suitable for closing off the vessel. The cap includes a fluidics system, which includes an inlet and an outlet. The inlet and the outlet are arranged to be in an interior volume of the vessel when the cap is closing off the vessel. The cap also includes a measurement region for optical microscopy, which includes a sample region suitable for the suspension. The sample region is in fluid connection with the fluidics system. The cap also includes a pump suitable for inducing a flow in the fluidics system. A particular monitoring system and setup is for monitoring cells in a cell culture liquid.

20 Claims, 3 Drawing Sheets

(51) Int. Cl.
   *G01N 21/00*    (2006.01)
   *B01L 3/00*     (2006.01)
   *C12M 1/00*     (2006.01)
   *C12M 1/34*     (2006.01)
   *G01N 21/84*    (2006.01)

(52) U.S. Cl.
   CPC ....... *B01L 3/502738* (2013.01); *C12M 23/38* (2013.01); *C12M 23/50* (2013.01); *C12M 41/36* (2013.01); *G01N 21/84* (2013.01); *B01L 3/50825* (2013.01); *B01L 2200/0647* (2013.01); *B01L 2300/042* (2013.01); *B01L 2300/046* (2013.01); *B01L 2300/0654* (2013.01); *B01L 2400/0481* (2013.01); *B01L 2400/0638* (2013.01)

(58) Field of Classification Search
   USPC ..... 422/50, 68.1, 82.05, 501, 502, 547, 550, 422/568, 129; 436/43, 164
   See application file for complete search history.

(56) References Cited

U.S. PATENT DOCUMENTS

| | | | |
|---|---|---|---|
| 2009/0296083 A1* | 12/2009 | Saaski et al. | 356/246 |
| 2009/0305393 A1* | 12/2009 | Joeris | 435/287.1 |
| 2012/0015391 A1* | 1/2012 | Zhang et al. | 435/29 |
| 2014/0038171 A1* | 2/2014 | Metzger et al. | 435/5 |

* cited by examiner

CAP FOR MONITORING OBJECTS IN SUSPENSION

CROSS-REFERENCE TO RELATED APPLICATIONS

This application is the U.S. National Phase of International Application No. PCT/EP2014/066312, filed Jul. 29, 2014, designating the U.S. and published in English as WO 2015/014858 on Feb, 5, 2015 which claims the benefit of European Patent Application No. 13178714.5, filed Jul. 31, 2013. Any and all applications for which a foreign or domestic priority claim is identified here or in the Application Data Sheet as filed with the present application are hereby incorporated by reference under 37 CFR 1.57.

TECHNICAL FIELD

The invention pertains to the technical field of observing and monitoring objects in suspension by microscopy. In particular, the present invention relates to a system and method for monitoring objects, e.g. cells, in suspension within a vessel, preferably by digital holographic microscopy.

BACKGROUND

Observing and monitoring microscopic objects in a suspension, such as cells in a bio-reactor, is a necessity in many present-day applications related to biology, chemistry, physics, environmental science, etc. A multitude of systems is known which allow such monitoring for specific applications.

Microscopic objects present in suspension in a vessel could be difficult to monitor by microscopy for a number of reasons, such as the continuous movement of the objects due to e.g. small currents in the suspension liquid, the opacity of the liquid or the size of the vessel. Usually, microscopy is performed on small samples. One possible way of monitoring objects in suspension in a storage vessel by microscopy is to manually take small samples from the suspension on a regular basis for viewing under a microscope. It is clear that such a manual procedure is not suitable for monitoring of a large number of suspensions located in a multitude of vessels.

One solution is to provide a transport system, which is capable of guiding the suspension towards a microscope. Such a transport system may take the form of a fluidics system, wherein typically a pumping mechanism transports the suspension from and, if desired, to the storage vessel. For instance, patent application US 2010/0315501 A1 discloses an electronic imaging flow-microscope for remote environmental sensing, bioreactor process monitoring, and optical microscopic tomography applications. Hereby, a fluid conduit has a port on each end of a thin flat transparent fluid transport region. A planar illumination surface contacts one flat side of the transparent fluid transport region and a planar image sensing surface contacts the other flat side. Light from the illumination surface travels through the transparent fluid transport region to the planar image sensing surface, producing a light field affected by the fluid and objects present. The planar image sensing surface creates electrical image signals responsive to the light field. The planar illumination surface can be light emitting elements such as LEDs, OLEDs, or OLET, whose illumination can be sequenced in an image formation process. The flow microscope can further comprise flow-restricting valves, pumps, energy harvesting arrangements, and power management. Although the use of such a fluidics system constitutes an improvement over manually taking samples in a large-scale monitoring set-up, there remains a problem of ensuring a connection of the fluidics system with the suspensions in the storage vessels. In fact, the fluidics system of US 2010/0315501 is suitable for long-time monitoring of the suspension in one specific vessel, but may be difficult to use in practice for monitoring or observing suspensions in a multitude of vessels using only one microscopic system. Furthermore, connecting such fluidics system to a vessel is a time-consuming manual process, which does not lend itself to be automated.

There remains a need in the art for an improved system and method for the observation or monitoring of objects in suspension in a vessel, which allows an automated observation or monitoring by a microscopic system of the suspensions in a multitude of vessels without a need of reconnecting fluidic tubing or the like. There remains a need in the art for an improved system and method for the observation or monitoring of objects in suspension in a vessel, whereby the vessel is closed off before, during and after the monitoring, thereby remaining sterile. There remains a need in the art for an improved vessel and cap which are cheap and easy to transport and store.

The present invention aims to resolve at least some of the problems mentioned above. The invention thereto aims to provide a cap for a vessel comprising a fluidics system which comprises a measurement region. The present invention also aims to provide a method and system for observing or monitoring a suspension in a vessel, suitable for monitoring suspensions in a multitude of vessels with one microscope.

SUMMARY

The present invention provides a vessel for storing and monitoring a suspension of microscopic objects, comprising a cap suitable for closing off the vessel, whereby the cap comprises a fluidics system comprising an inlet and an outlet, said inlet and said outlet arranged to be in an interior volume of said vessel when the cap is closing off said vessel, whereby said cap comprises a measurement region for optical microscopy which comprises a sample region suitable for said suspension, the sample region in fluid connection with said fluidics system, whereby said cap comprises pumping means suitable for inducing a flow in said fluidics system.

Preferably, said cap comprises a gas exchange system for allowing gas exchange between the interior of the vessel and the environment. A vessel with such a cap can be used in an incubator.

The present invention further provides a cap suitable for, preferably arranged for, closing off said vessel and a vessel suitable for, preferably arranged for, being closed off by said cap.

Hereby and throughout this document, it should be noted that the cap comprises the fluidics system, which means that the fluidics system is part of the cap, rather than a separate system attached to the cap.

Note that the inlet and the outlet of the fluidics system are suitable and prefereably arranged to be in the interior volume of said vessel when the cap is closing off said vessel, meaning that when the cap is closing off the vessel, both inlet and outlet are located within the interior volume of the vessel. As a result, a closed fluidics circuit is obtained which is comprised within the closed off vessel. If the cap is not closing off the vessel, the inlet and outlet of the fluidics system, which is part of the cap, is not necessarily inside the interior of the vessel. Preferably, the cap comprises a top surface which is smooth and/or essentially free from protrusions arising from the fluidics system, and preferably the cap comprises an essentially cylindrical exterior side surface. In an alternative embodiment, a number of protrusions and/or recesses are provided on the top and/or the exterior side surface of the cap in order to detect the orientation of the cap, in particular the position of the sample region.

In a further aspect, the present invention provides a system for monitoring a suspension in a vessel, comprising a vessel and a vessel turning system, whereby said vessel comprises a cap which is suitable for closing off the vessel and whereby said vessel turning system is suitable for turning over said vessel, whereby said cap comprises a fluidics system comprising an inlet and preferably an outlet, said inlet and said outlet arranged to be in fluid connection with an interior volume of said vessel when the cap is closing off said vessel, whereby said cap comprises a measurement region for optical microscopy which comprises a sample region for said suspension which is in fluid connection with said fluidics system.

In yet a further aspect, the present invention provides a system for monitoring a suspension in a vessel, comprising a vessel as disclosed in this document, and a microscopic system suitable for obtaining measurements at the position of the measuring region of the cap of the vessel.

Furthermore, the present invention provides for a method for observing or monitoring a suspension in a vessel, comprising the steps of:
providing a vessel as disclosed in this document, said vessel comprising a suspension and closed off with the cap of the vessel;
arranging a microscopic system for obtaining measurements at the position of the measuring region of said cap;
bringing at least part of said suspension to the sample region of the cap, such as by pumping or by turning over said vessel, e.g. by a vessel turning system; and
obtaining information about said suspension in said sample region by said microscopic system.

The present invention also provides the use of a vessel, a cap, a system and/or a method as disclosed in this text for monitoring cells in a suspension, preferably cells in a cell culture liquid.

DETAILED DESCRIPTION OF CERTAIN EMBODIMENTS

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

In a first aspect, the invention provides a vessel for storing and monitoring a suspension of microscopic objects, comprising a cap suitable for closing off the vessel, whereby the cap comprises a fluidics system comprising an inlet and an outlet, said inlet and said outlet arranged to be in an interior volume of said vessel when the cap is closing off said vessel, whereby said cap comprises a measurement region for optical microscopy which comprises a sample region suitable for said suspension, the sample region in fluid connection with said fluidics system, whereby said cap comprises pumping means suitable for inducing a flow in said fluidics system.

In an embodiment, the vessel and/or the cap comprises identification means, such as an RFID tag, for unique identification and for automated traceability and/or reporting of measurements.

In an embodiment, the fluidics system comprises a number of channels, tubes or ducts which are integrated within the cap.

In an embodiment, the fluidics system comprises a dilution system to address high particle density ranges.

In an embodiment, the cap is arranged for closing off the vessel. The cap may be disconnected or connected to the vessel. The cap may be at least partially removably connected to the vessel, e.g. the cap may be of the screw-cap type, the stopper type, the clasp type or the flip-open type.

The measurement region comprises a sample region which is suitable for, capable of or arranged for holding at least a sample of said suspension. Furthermore the measurement region may comprise other elements which may improve the monitoring or observation of the suspension, such as disclosed later in this document. The sample region is in fluid connection with the fluidics system in order to be capable of receiving a sample of a suspension via the fluidics system coming from the interior of the vessel. Such a suspension may flow from the interior volume of the vessel to the sample region and back to the interior volume, because of the work done by the pumping means of the cap. In an embodiment, the pumping means are at least partly integrated within the cap, e.g. in the case the pumping means comprise a plunger system.

In a preferred embodiment, the sample region comprises a transparent surface, making it easier to directly observe the microscopic objects in suspension which are present in the sample region.

In a preferred embodiment, the measurement region comprises light guiding means such as a mirror or a lens, arranged for guiding a light beam from an incoming direction towards said sample region and further towards an outgoing direction. Such light-guiding means may allow for easier measurement, in particular in automated monitoring set-ups wherein some tolerance should be provided as to the orientation of the vessel of the present invention with respect to the monitoring system. In a particularly preferred embodiment, the vessel, and preferably the cap of the vessel, comprises orientation means such as a marker, a protrusion or a recess in order to allow, preferably automated, detection of the orientation of the cap, in particular of the position of the sample region.

In a preferred embodiment, the pumping means comprise a membrane mounted on said fluidics system of said cap and one or more valves in said fluidics system, said membrane and valves suitable for inducing a flow in said fluidics system in a predetermined direction when the membrane is being pulled or pushed in order to change an interior volume of the fluidics system.

In a preferred embodiment, the pumping means comprise an actuation element attached to said membrane, said actuation element arranged to pull or push said membrane under the influence of external energy providing means, preferably whereby the actuation element comprises magnetic material and said external energy providing means comprise a generator of a variable magnetic field.

In a preferred embodiment, the vessel comprises a suspension and/or the cap is closing off said vessel.

In a preferred embodiment, said cap comprises optical, preferably micro-optical, components such as lenses, mirrors and/or one or more optical fibers for guiding light from an illumination source to the sample region and/or from the sample region to a camera sensor.

In a preferred embodiment, the cap comprises at least part of a microscopic observation system. Preferably, said cap comprises a micro-optical system. Said micro-optical system may comprise:
  a camera sensor embedded in said cap;
  an illumination means embedded in said cap, and/or
  a, preferably lensless, digital holography system embedded in said cap.

Said digital holography system may comprise a differential holography system. In a more preferred embodiment, the cap comprises data transmission means for transmitting data obtained by said microscopic observation system to an external data processing system. Said transmission means may comprise wired transmission means and/or wireless transmission means.

Preferably said cap comprises an illumination source which is embedded in the cap. In a preferred embodiment, said illumination source comprises a partially coherent light source, such as a LED, and/or a coherent light source, such as a laser.

In a more preferred embodiment, said cap comprises a power source for powering active components of the cap such as an illumination source, a digital holography system and/or a camera sensor. Alternatively or additionally, said cap comprises a power inlet for connecting active components of the cap with an external power source.

The present invention further provides a cap suitable for closing off a vessel as described in this text, in particular a cap comprising a fluidics system comprising an inlet and an outlet, said inlet and said outlet suitable for being inserted into an interior volume of said vessel when the cap is closing off said vessel, whereby said cap comprises a measurement region for optical microscopy which comprises a sample region suitable for said suspension, the sample region in fluid connection with said fluidics system, whereby said cap comprises pumping means suitable for inducing a flow in said fluidics system.

The present invention also provides a vessel which is adapted to be closed off by such a cap.

In a further aspect, the present invention provides a system for monitoring a suspension in a vessel, comprising a vessel and a vessel turning system, whereby said vessel comprises a cap which is suitable for closing off the vessel and whereby said vessel turning system is suitable for turning over said vessel, whereby said cap comprises a fluidics system comprising an inlet and preferably an outlet, said inlet and said outlet arranged to be in fluid connection with an interior volume of said vessel when the cap is closing off said vessel, whereby said cap comprises a measurement region for optical microscopy which comprises a sample region for said suspension which is in fluid connection with said fluidics system. Preferably said system comprising a microscopic system suitable for obtaining measurements at the position of the measuring region of the cap.

In yet a further aspect, the present invention provides a system for monitoring a suspension in a vessel, comprising a vessel as disclosed in this document, and a microscopic system suitable for obtaining measurements at the position of the measuring region of the cap of the vessel.

In a preferred embodiment, the system comprises external energy providing means for actuating the pumping means of said cap, preferably whereby said external energy providing means comprise a generator of variable magnetic fields and said pumping means comprise an actuation element comprising magnetic material.

In a preferred embodiment, said system comprises controlling means for controlling said microscopic system and/or said external energy providing means, whereby preferably said controlling means are arranged to control said microscopic system and/or said external energy providing means taking into account data related to said suspension measured by said microscopic system.

Furthermore, the present invention provides for a method for observing or monitoring a suspension in a vessel, comprising the steps of:
  providing a vessel as disclosed in this document, said vessel comprising a suspension and closed off with the cap of the vessel;

arranging a microscopic system for obtaining measurements at the position of the measuring region of said cap;

bringing at least part of said suspension to the sample region of the cap, such as by pumping or by turning over said vessel, e.g. by a vessel turning system; and obtaining information about said suspension in said sample region by said microscopic system.

In an embodiment, said microscopic system is at least partly embedded in said cap.

In an embodiment, said information is obtained continuously, in packages and/or at request.

In an embodiment, said information is transmitted wirelessly or via wired, preferably to an external data processing system. In a preferred embodiment, said information is obtained by a camera sensor embedded in said cap and transmitted wirelessly or via wired, preferably to an external data processing system. In a preferred embodiment, said information is transmitted continuously, in packages and/or at request.

In an embodiment, the method comprises the step of pumping suspension and/or other fluid through said fluidics system before and/or after said step of obtaining information about said suspension in said sample region by said microscopic system.

In a preferred embodiment, the information is obtained during said pumping.

The present invention also provides for a method for observing and monitoring a suspension in a vessel, comprising the steps of:

providing a vessel closed off by a cap comprising a fluidics system comprising an inlet and preferably an outlet, said inlet and said outlet in fluid connection with an interior volume of said vessel, whereby said cap comprises a measurement region for optical microscopy which comprises a sample region for said suspension which is in fluid connection with said fluidics system, whereby said vessel comprises a suspension;

bringing at least part of said suspension to the sample region via said fluidics system by turning over said vessel, preferably by a vessel turning system;

arranging a microscopic system for obtaining measurements at the position of the measuring region of the cap, preferably when the vessel is in a turned-over position;

obtaining information about said suspension in said sample region by said microscopic system.

The present invention also provides the use of a vessel, a cap, a system and/or a method as disclosed in this text for monitoring cells in a suspension, preferably cells in a cell culture liquid.

The invention is further described by the following non-limiting examples which further illustrate the invention, and are not intended to, nor should they be interpreted to, limit the scope of the invention.

The present invention will be now described in more details, referring to examples that are not limitative.

It is supposed that the present invention is not restricted to any form of realization described previously and that some modifications can be added to the presented example of fabrication without reappraisal of the appended claims.

EXAMPLES

Figure 1:
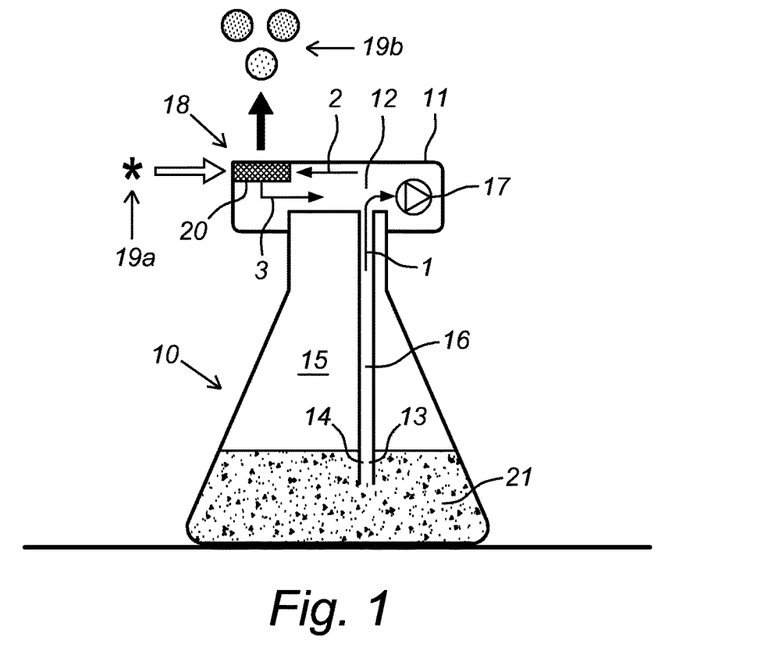
FIG. 1 illustrates schematically an embodiment of a vessel comprising a cap with pumping means and a method for monitoring a suspension according to the present invention.

FIG. 1 illustrates schematically an embodiment of a vessel comprising a cap with pumping means and a method for monitoring a suspension according to the present invention. A vessel (10) comprises a cap (11). In FIG. 1, the cap (11) closes off the vessel (10). The cap comprises a fluidics system (12) which comprises an inlet (13) and an outlet (14) in fluid connection with an interior volume (15) of the vessel (10) when the cap (11) closes off the vessel (10). The inlet (13) and outlet (14) are here shown as connected to a single tube (16), but it should be clear that the tube (16) may be subdivided in at least an inlet tube and an outlet tube. The cap (11) further comprises pumping means (17) connected to the fluidics system (12). The cap also comprises a measurement region (18) for optical microscopy (19a,19b), the measurement region (18) comprising a sample region (20) which is in fluid connection with the fluidics system (12).

An embodiment of the method for monitoring a suspension according to the present invention is also illustrated in FIG. 1. Hereby, a vessel (10) comprising a suspension (21) of e.g. cells in a liquid culture medium, is closed off by a cap (11). A microscopic system (19a,19b) is arranged at the position of the measuring region (18) of the cap (11). A part of the suspension (21) is pumped (1) by the pumping means (17) from the interior (15) of the vessel via the inlet (13) towards (2) the sample region (20) of the cap (11). A microscopic image or other microscopic information may than be obtained about the suspension in the sample region (20). The suspension can then be pumped back (3) from the sample region to the interior (15) of the vessel (10) via the outlet (14). This method can be performed in continuous mode, thereby performing real-time inline microscopic monitoring of the suspension. In this example, the microscopic system is a color digital holographic microscope, whereby light of a light source (19a) is used to illuminate the sample region (20), the transmitted and/or reflected light being guided e.g. by light-guiding means such as a slanted mirroring surface in the measurement region (18), towards the recording means (19b), e.g. a CCD camera, of the microscopic system. Other microscopic systems and methods may be used. Preferred systems and methods are digital holographic microscopy systems or methods, including differential digital holographic microscopy or doubly differential digital holographic microscopy as disclosed in documents US2012200901A1, WO2012062805A1, EP2357539A1,US2011141273A1,US2008018966A1, EP1631788A1,US2004156098A1,EP1524491A1, EP1321760A1 or US2002159047A1.

Figure 2:
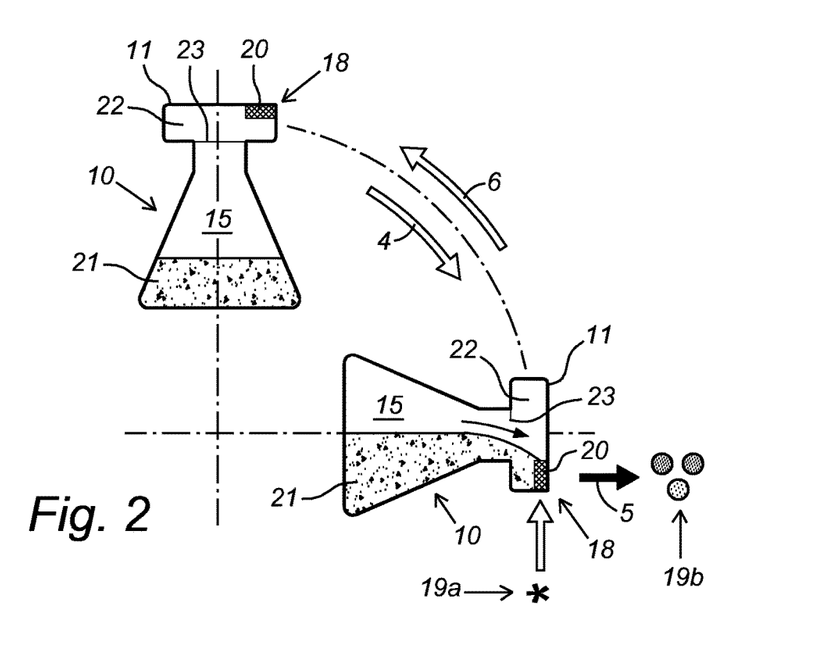
FIG. 2 illustrates schematically another embodiment of a vessel and a method for monitoring a suspension according to the present invention.

FIG. 2 illustrates schematically another embodiment of a vessel and a method for monitoring a suspension according to the present invention. A vessel (10) comprises a cap (11). In FIG. 2, the cap (11) closes off the vessel (10). The cap comprises a fluidics system which comprises an inlet and preferably an outlet in fluid connection with an interior volume (15) of the vessel (10) when the cap (11) closes off the vessel (10). The inlet and outlet and the fluidics system are not explicitly shown here, but the fluidics system may comprise tubes inside the cap or may comprise the hollow interior of the cap (22), and the inlet and outlet may be openings in the bottom (23) of the cap (11), thereby ensuring that the fluidics system is in fluid connection with the interior (15) of the vessel when the cap (11) is closing off the vessel. The cap also comprises a measurement region (18) for optical microscopy, the measurement region (18) comprising a sample region (20) which is in fluid connection with the fluidics system.

An embodiment of the method for monitoring a suspension according to the present invention is also illustrated in FIG. 2. Hereby, a vessel (10) comprising a suspension (21) is closed off by a cap (11). The vessel is subsequently turned over (4) such that the suspension flows into the sample region (20) of the measurement region (18). A microscopic system (19a,19b) is arranged at the position of the measurement region (18) and microscopic information is obtained (5) about the suspension in the sample region (20). The vessel suspension can then be turned back (6), thereby allowing the suspension to flow back into the interior (15) of the vessel. In this example, the microscopic system is a color digital holographic microscope, whereby light of a light source (19a) is used to illuminate the sample region (20), the transmitted and/or reflected light being guided e.g. by light-guiding means such as a slanted mirroring surface in the measurement region (18), towards the recording means (19b), e.g. a CCD camera, of the microscopic system. Other microscopic systems and methods may be used. Preferred systems and methods are digital holographic microscopy systems or methods, including differential digital holographic microscopy or doubly differential digital holographic microscopy as disclosed in documents US2012200901A1, WO2012062805A1,EP2357539A1, US2011141273A1,US2008018966A1, EP1631788A1, US2004156098A1,EP1524491A1,EP1321760A1 or US2002159047A1.

Figure 3:
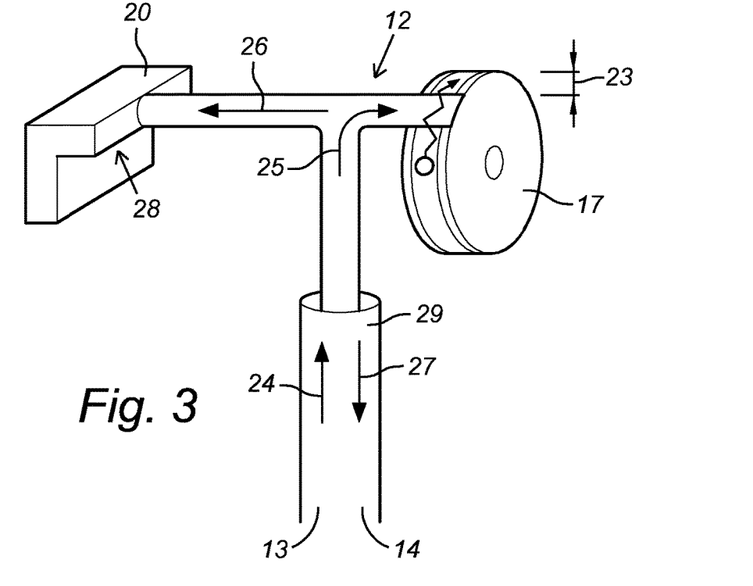
FIGS. 3 and 4 illustrate in more detail an embodiment of the fluidics system of a vessel and cap according to the present invention.
Figure 4:
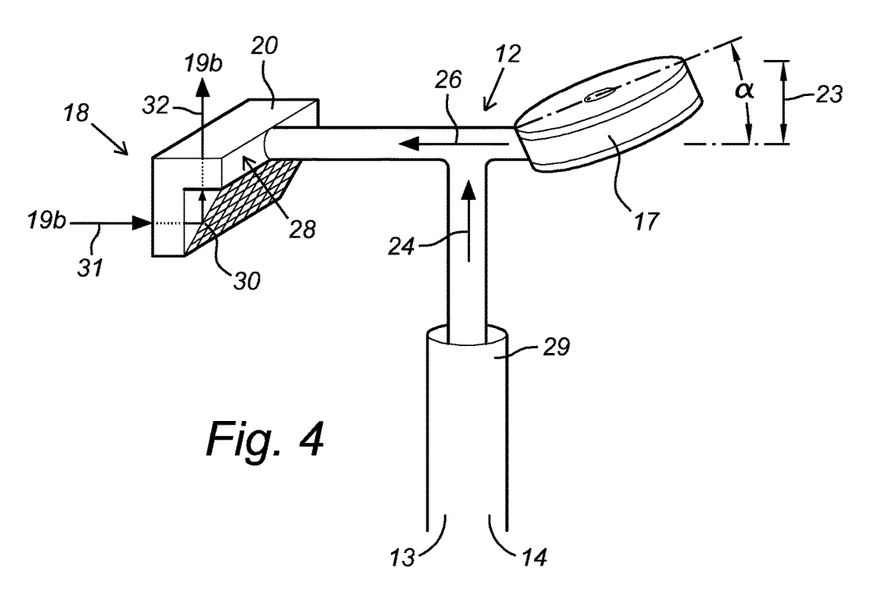

FIGS. 3 and 4 illustrate in more detail an embodiment of the fluidics system of a vessel and cap according to the present invention. The fluidics system (12) herein comprises pumping means (17). In a preferred embodiment, the pumping means (17) are arranged such that when the cap is closing off the vessel and the vessel is standing straight, the pumping means comprise a volume in fluid connection with the fluidics system which is located above the rest of the fluidics system (23). The pumping means are thus arranged that possible gas bubbles present in the suspension flowing through the fluidics system can be evacuated, preferably before the bubbles reach the sample region. In this example, the evacuation can be done by an evacuation system in the pumping means, e.g. a hole or a gas-permeable, liquid-impermeable membrane. In FIGS. 3 and 4, the fluidics system (12) may comprise tubing leading from the inlet (13) to the pumping means (24, 25), further (26) to the sample region (20), and then preferably back (27) to the interior of the vessel via the outlet (14). Mark that the tubings showing in FIGS. 3 and 4 may be subdivided into separate parts for e.g. the incoming and outgoing flows of suspension with respect to the sample region. Alternatively, the outlet may be located (28) near the sample region, such that the suspension still flows back to the interior of the vessel if the cap is closing off the vessel. In another alternative, the pumping means (17) comprise a plunger system (29). The pumping means may be actuated manually or automatically.

FIG. 4 also shows an embodiment wherein the measurement region (18) light-guiding means comprise a slanted mirroring surface (30) for reflecting the light coming from illumination means (19a) from an incoming direction (31) towards an outgoing direction (32) to the recording means (19b) of the microscopic system. In the illustrated setup, the microscopic information is obtained in transmission mode, wherein the light transmitted through the sample region is being recorded and preferably analysed to obtain information on the suspension in the sample region.

Figure 5:
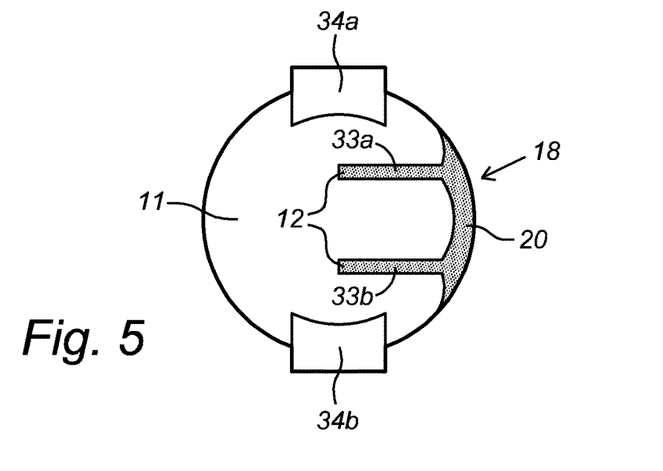
FIG. 5 illustrates a top view on a cap of a vessel according to the present invention.

FIG. 5 illustrates a top view of an embodiment of a cap of a vessel according to the present invention. The cap (11) comprises a fluidics system (12) which comprises ducts (33a,33b) in fluid connection with the sample region (20) in the measurement region (18). A first duct (33a) may serve as an inlet duct if the pumping means are actuated, whereby a suspension may flow from the vessel's interior to the sample region; a second duct (33b) may serve as an outlet duct if the pumping means are actuated, whereby the suspension may flow from the sample region back towards the vessel's interior. The pumping means in FIG. 5 comprise a membrane pumping system (34a,34b) which can be activated mechanically and electronically. Mechanical actuation can be performed manually or in an automated manner, e.g. by pushing spring-loaded buttons (34a) or (34b), at least one of which is connected to a membrane, the membrane being arranged to change the volume of the fluidics system when being pulled or pushed. In this case the membrane may form part of the wall of the fluidics system (12). By repeatedly pushing the buttons (34a) or (34b), a flow can be induced in the fluidics system, whose direction can be determined by e.g. one or more valves present in the fluidics system. Additionally, the membrane can also be electrically activated, e.g. if a magnetic element such as a magnetic plate is attached to the membrane and a magnetic field is induced and varied at the location of the membrane. The presence of both mechanical and electrical pumping means allows the use of the vessel and cap in both small-scale laboratory microscopy set-ups, whereby the suspension can be pumped to the sample region manually, and in large-scale automated testing set-ups, whereby an automated set-up is capable of accepting a vessel, actuating the pumping means electrically or mechanically, and observing the suspension in the sample region by an automated microscopic system.

Figure 6:
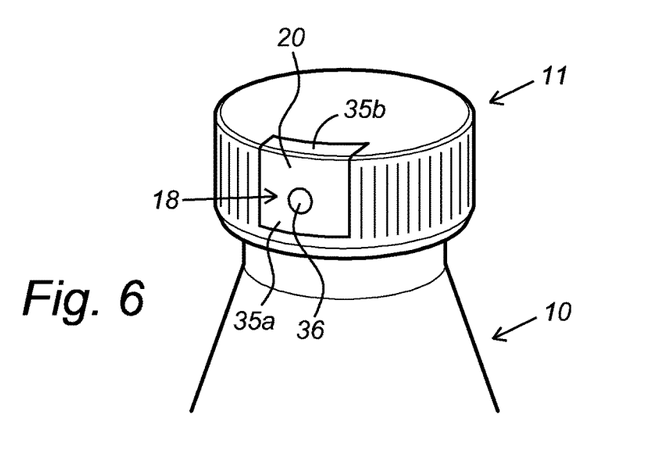
FIG. 6 shows a perspective view on a vessel and a cap according to the present invention.

FIG. 6 shows a perspective view of a vessel and a cap according to the present invention. The cap (11) closes off the vessel (10), the cap comprising a measurement region (18) which comprises a sample region (20). The sample region (20) comprises a first transparent surface (35a) at the side of the cap and a second transparent region (35b) at the top of the cap, through which a microscopic measurement can be performed. The transparent surfaces may comprise a region specifically adapted to allow a microscopic measurement (36). Such a region (36) may comprise a flat surface wall, specific transparency properties such as increased or decreased transparency at specific wavelengths, an optical filter, a lens integrated in the surface, etc.

Figure 7:
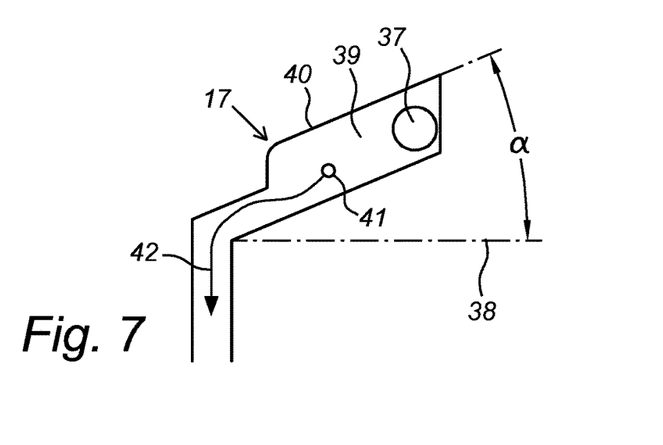
FIG. 7 illustrates the orientation of the pumping means in an embodiment of the present invention.

FIGS. 4 and 7 illustrate the orientation of the pumping means in an embodiment of the present invention. In a preferred embodiment of the invention, the pumping means are arranged such that possible gas bubbles (37) present in the suspension flowing through the fluidics system can be evacuated, preferably before the bubbles reach the sample region. This is illustrated in detail in FIG. 7 where a gas bubble (37) has migrated to the top of the pumping means (17). It should be noted that the pumping means are integrated in the cap under an angle α in FIG. 7, this angle taken with respect to a horizontal direction (38) and in the situation when the cap is placed on a vessel and the vessel is placed on a horizontal surface. In a preferred embodiment, the fluidics system comprises a gas reservoir for collecting possible gas bubbles which enter the fluidics system, preferably the gas reservoir is arranged between the inlet and the sample region such that gas bubbles are prevented from entering the sample region where the measurement is taken, and preferably the gas reservoir located above other components, in particular other ducts or reservoirs, of the fluidics system. In the embodiment illustrated in FIG. 7, the pumping means (17) comprise such a gas reservoir (39), the reservoir comprising a membrane wall (40). The embodiment shown in FIG. 7 has the further advantage that objects (41), e.g. cells, in the suspension may sediment (42) towards e.g. the vessel's interior. Thus, after a measurement, when the pumping has stopped, all objects in the suspension may flow down to the interior of the vessel. This could be important in the case of the vessel being a bioreactor wherein the suspension is a cell culturing liquid.

What is claimed is:

1. A vessel for storing and monitoring a suspension of microscopic objects, comprising a cap configured to close off the vessel,
    wherein the cap comprises a fluidics system comprising an inlet and an outlet, said inlet and said outlet arranged to be in an interior volume of said vessel when the cap is closing off said vessel,
    wherein said cap comprises a measurement region for optical microscopy which comprises a sample region suitable for said suspension, the sample region in fluid connection with said fluidics system, and
    wherein said cap comprises a pump configured to induce a flow in said fluidics system.

2. The vessel according to claim 1, wherein said sample region comprises a transparent surface.

3. The vessel according to claim 1, wherein said measurement region comprises a guide for light configured to guide a light beam from an incoming direction towards said sample region and further towards an outgoing direction.

4. The vessel according to claim 1, wherein said pump comprises a membrane mounted on said fluidics system of said cap and one or more valves in said fluidics system, said membrane and valves configured to induce a flow in said fluidics system in a predetermined direction when the membrane is being pulled or pushed in order to change an interior volume of the fluidics system.

5. The vessel according to claim 1, wherein said pump comprises an actuation element attached to said membrane, said actuation element arranged to pull or push said membrane under the influence of an external energy provider.

6. The vessel according to claim 1, wherein said vessel comprises a suspension and/or wherein said cap is closing off said vessel.

7. A cap for closing off a vessel that is for storing and monitoring a suspension of microscopic objects, the cap comprising a fluidics system comprising an inlet and an outlet, said inlet and said outlet configured to be inserted into an interior volume of said vessel when the cap is closing off said vessel, wherein said cap comprises a measurement region for optical microscopy which comprises a sample region suitable for said suspension, the sample region in fluid connection with said fluidics system, and wherein said cap comprises a pump configured to induce a flow in said fluidics system.

8. A system for monitoring a suspension in a vessel, comprising: the vessel according to claim 1, and a microscopic system configured to obtain measurements at a position of the measurement region of the cap of the vessel.

9. The system according to claim 8, comprising: an external energy provider for actuating the pump of said cap.

10. A method for observing or monitoring a suspension in a vessel, comprising:
    providing the vessel according to claim 1, said vessel comprising a suspension and closed off with the cap of the vessel;
    arranging a microscopic system for obtaining measurements at a position of the measurement region of said cap;
    pumping at least part of said suspension to the sample region of the cap; and
    obtaining information about said suspension in said sample region by said microscopic system.

11. The method according to claim 10, further comprising pumping suspension and/or other fluid through said fluidics system before and/or after said obtaining information about said suspension in said sample region by said microscopic system.

12. The method according to claim 10, wherein said information is obtained during said pumping.

13. A system for monitoring a suspension in a vessel, comprising a vessel and a vessel turning system,
    wherein said vessel comprises a cap which is configured to close off the vessel,
    wherein said vessel turning system is configured to turn over said vessel,
    wherein said cap comprises a fluidics system comprising an inlet and optionally an outlet, said inlet and said optional outlet arranged to be in fluid connection with an interior volume of said vessel when the cap is closing off said vessel, and
    wherein said cap comprises a measurement region for optical microscopy which comprises a sample region for said suspension which is in fluid connection with said fluidics system.

14. A method for observing and monitoring a suspension in a vessel, comprising:
    providing a vessel closed off by a cap comprising a fluidics system comprising an inlet and optionally an outlet, said inlet and said optional outlet in fluid connection with an interior volume of said vessel, wherein said cap comprises a measurement region for optical microscopy which comprises a sample region for said suspension which is in fluid connection with said fluidics system, and wherein said vessel comprises a suspension;
    bringing at least part of said suspension to the sample region via said fluidics system by turning over said vessel;
    arranging a microscopic system for obtaining measurements at a position of the measurement region of the cap; and
    obtaining information about said suspension in said sample region by said microscopic system.

15. The vessel according to claim 5, wherein the actuation element comprises a magnetic material and said external energy provider comprises a generator of a variable magnetic field.

16. The system according to claim 9, wherein said external energy provider comprise a generator of variable magnetic fields and said pump comprise an actuation element comprising a magnetic material.

17. The system according to claim 9, wherein said system comprises a controller for controlling said microscopic system and/or said external energy provider.

18. The system according to claim 17, wherein said controller is configured to control said microscopic system and/or said external energy provider taking into account data related to said suspension measured by said microscopic system.

19. The method according to claim 14, wherein said at least part of said suspension is brought to the sample region via said fluidics system by turning over said vessel by a vessel turning system.

20. The method according to claim 14, wherein said microscopic system for obtaining measurements is arranged at a position of the measurement region of the cap when the vessel is in a turned-over position.

* * * * *

UNITED STATES PATENT AND TRADEMARK OFFICE
CERTIFICATE OF CORRECTION

PATENT NO. : 9,675,974 B2  
APPLICATION NO. : 14/909046  
DATED : June 13, 2017  
INVENTOR(S) : Serge Jooris et al.

It is certified that error appears in the above-identified patent and that said Letters Patent is hereby corrected as shown below:

On the Title Page

In Column 2 (Primary Examiner) at Line 1, Change "Brian J Sine" to --Brian J Sines--.

In the Specification

In Column 1 at Line 9, Change "designing" to --designating--.

In Column 1 at Line 10, Change "Feb," to --Feb.--.

In Column 2 at Line 62, Change "prefereably" to --preferably--.

In the Claims

In Column 11 at Line 21 (approx.), In Claim 3, change "light" to --light,--.

Signed and Sealed this  
Twenty-fourth Day of October, 2017

Joseph Matal  
*Performing the Functions and Duties of the*  
*Under Secretary of Commerce for Intellectual Property and*  
*Director of the United States Patent and Trademark Office*